United States Patent [19]
Phillips et al.

[11] Patent Number: 5,122,362
[45] Date of Patent: Jun. 16, 1992

[54] METHODS AND COMPOSITIONS FOR THE MEASUREMENT OF GLUCOSE TOLERANCE

[75] Inventors: William T. Phillips; Joyce G. Schwartz, both of San Antonio, Tex.

[73] Assignee: Board of Regents, The University of Texas System, Austin, Tex.

[21] Appl. No.: 445,884

[22] Filed: Dec. 4, 1989

[51] Int. Cl.$^5$ .......................................... G01N 31/00
[52] U.S. Cl. ........................................ 424/9; 514/866
[58] Field of Search ............................ 424/9; 514/866

[56] References Cited

U.S. PATENT DOCUMENTS 4,073,910  2/1978  Kawashima et al. ................. 514/337
4,689,219  8/1987  Sugden .................................. 424/80

OTHER PUBLICATIONS

Hansen, Karen-Investigations into the Blood Sugar in Man *Acta Med. Seand Supp.* 4:585-593 (1923).
Brener, W. et al., Regulation of the Gastric Emptying of Glucose *Gastroenterology* 85:76-82 (1983).
Liddle, R. A. et al., Physiological Role for CCK in Reducing Postprandial Hperglycemia in Humans *J. Clin. Invest* 81:1675-1681 (1988).
Massé J. (1990), *Clin. Chem.*, 36:819.
Palacios et al., (1989), *Dig. Dis. Sci.*, 34:385-389.
Malmud et al., (1982), *Sem. Nucl. Med.*, 12:116-125.
Puyn, U. and Gladtke, E. (1977), *Mschr. Kinderheilk.*, 125:147-152 (English translation).
Toeller et al., (1973), *Diabetologia*, 9:102-107.
Busick, E. J., "Natural History and Diagnosis", *Clinical Diabetes Mellitus*, pp. 32-42 (1982) G. P. Kozak Ed., W. B. Saunders Co., Philadelphia, Pa.
Davidson, J. K., Chapter 9 entitled "Diagnosis of Diabetes Mellitus", *Clinical Diabetes Mellitus*, pp. 90-107, 1986, Published by Thiame Inc., N.Y., N.Y.
Chandalia et al., article entitled "Diagnosis of Diabetes; The Size and Nature of Carbohydrate Load", *Diabetes*, (1970) 19:863-869.
Sisk et al., article entitled "Comparison of the 50 and 100 Gram Oral Glucose Tolerance Test", *Diabetes* (1970) 19:852-862.
Harano et al., article, "Usefulness of Maltose for Testing Glucose Tolerance", *Amer. J. Clin. Nutri* (1977) 30:924-931.
Hall et al., article, "The Effect of Bran on Glucose Kinetics and Plasma Insulin in Non-Insulin-Dependent Diabetes Mellitus", Diabetes Care (1980) 3:520-525.
Reed, B. D., article, "Screening for Gestational Diabetes—Analysis by Screening Criteria", *J. Family Pract.* (1984) 19:751-755.
Verza et al., article, "Hypertension in the Elderly is Associated With Impaired Glucose Metabolism Independently of Obesity and Glucose Intolerance", J. Hypertension (1988) 6(suppl 1): 545-548.

(List continued on next page.)

*Primary Examiner*—Glennon H. Hollrah
*Assistant Examiner*—Gary E. Hollinden
*Attorney, Agent, or Firm*—Arnold, White & Durkee

[57] ABSTRACT

The present invention provides methods and compositions for measuring glucose tolerance in a subject. The methods are useful in a variety of contexts, such as in the diagnosis of diabetes in both human and animal subjects, in assessing gastric emptying times, and even in the diagnosis of insulin resistance. It is proposed that the methods of the present invention will prove to be of particular use in the mass screenings of population, e.g., in screening for type II diabetes mellitus, due to its simplicity and reproducibility. The method is even adaptable to simple finger stick analysis. The invention method includes the use of a potable beverage containing a low total loading dose of glucose in a low osmolar solution. The oral glucose solutions of the present invention empty rapidly from the stomach, thereby eliminating the nausea and vomiting typically associated with oral glucose tolerance tests. The oral glucose solutions of the present invention provide a provide excellent reproducibility of results and a distinct separation between nondiabetic and diabetic subjects, thereby enabling clinicians to better diagnose diabetes in a subject.

22 Claims, 5 Drawing Sheets

OTHER PUBLICATIONS

Nelson. R. L., article, "Subspeciallty Clinics: Endocrinology", *Mayo Clin. Proc.* (1988) 63:263–269.

Reaven, G. M., Banting Lecture 1988: Role of Insulin Resistance in Human Disease, *Diabetes*, (1988) 37:1595–1607.

Singer et al., "Tests of Glycemia in Diabetes Mellitus; Their Use in Establishing a Diagnosis and in Treatment", *Ann Intern Med.*, (1989) 110:125–137.

Foster, D. W., "Insulin Resistance—A Secret Killer?", *N. Engl. J. Med.*, (1989) 320:(11):733–734.

Fackelmann, K. A., "Hidden Heart Hazards; Do High Blood Insulin Levels Foretell Heart Disease?", *Science News*, 136:184–186 (1989).

Schwartz et al., "Revision of the Oral Glucose Tolerance Test: A Pilot Study", *Clin. Chem.*, (1989) 35:1–8.

Phillips et al., article "Prospects for an Accurate, Reproducible Oral Glucose Tolerance Test", Submitted for publication to *Diabetes* in Nov. 1989.

A

B

C

D

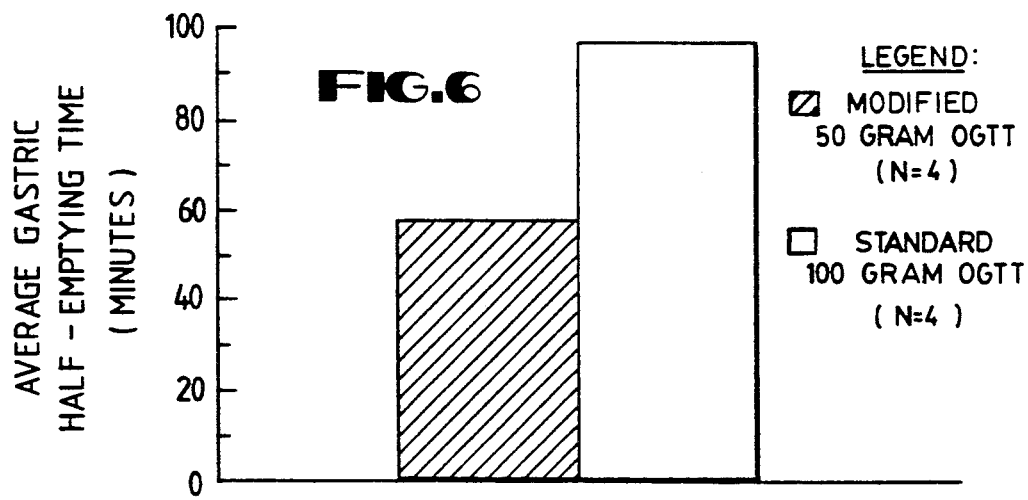
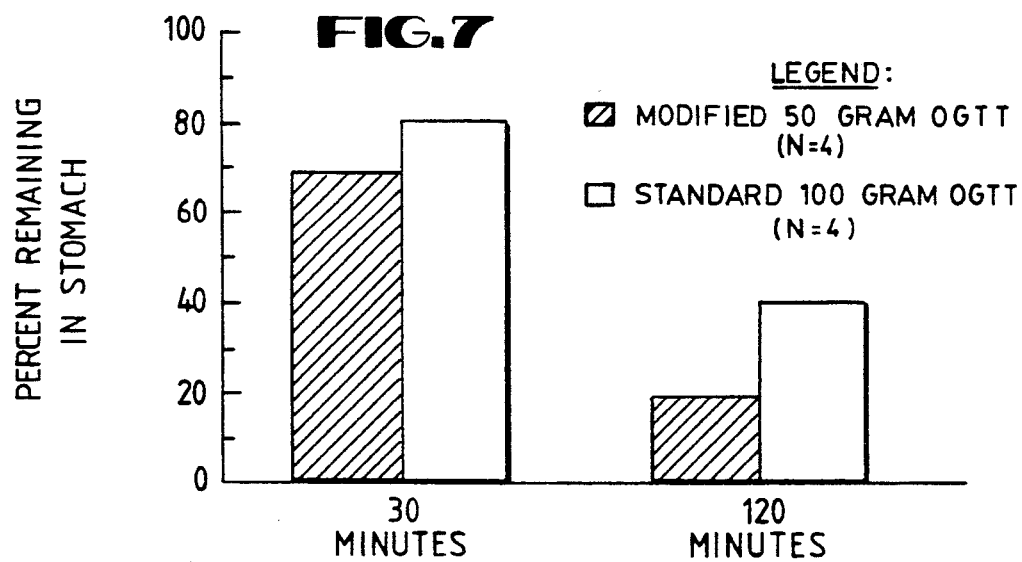
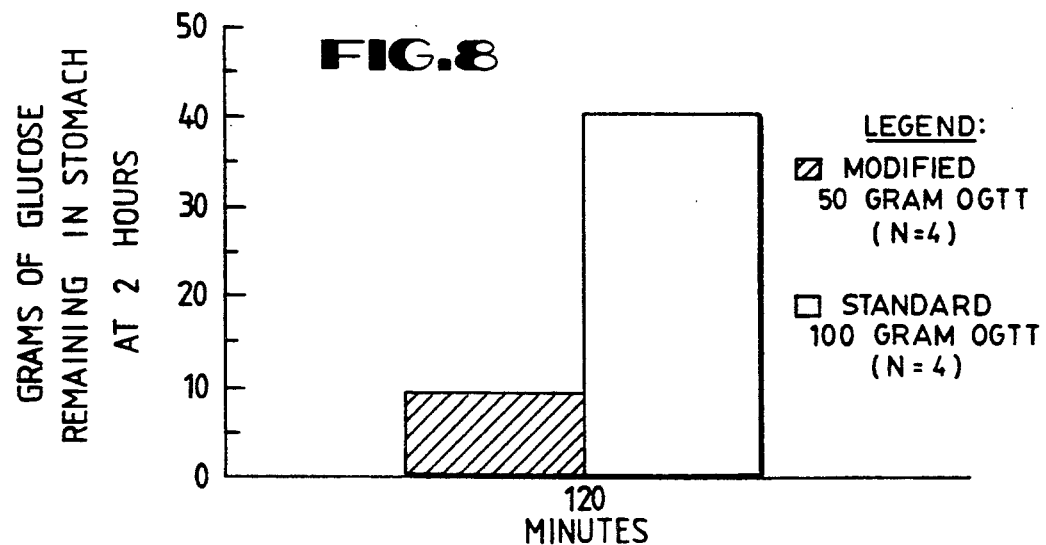

METHODS AND COMPOSITIONS FOR THE MEASUREMENT OF GLUCOSE TOLERANCE

BACKGROUND OF THE INVENTION

A. Field On The Invention

The present invention relates generally to methods and compositions for measuring glucose tolerance, such as in connection with oral glucose tolerance tests for the diagnosis of diabetes mellitus and other conditions relating to the body's response to serum glucose levels. In more particular aspects, the invention relates to an improved method for diagnosing diabetes mellitus which includes the use of a potable beverage containing a relatively low molar concentration and total loading dose of glucose.

B. Description Of Related Art

Diabetes mellitus is a disease characterized by hyperglycemia occurring from a relative or absolute decrease in insulin secretion decreased insulin sensitivity or insulin resistance. The morbidity and mortality of this disease result from vascular, renal, and neurological complications.

An oral glucose tolerance test is a clinical test used to diagnose diabetes. In an oral glucose tolerance test, a patient's physiological response to a glucose load or challenge is evaluated. Generally, in an adult patient about 2 grams of glucose is administered for each kilogram of body weight, in children the amount is relatively less, being about 1.75 grams per kilogram body weight. The glucose load is administered to the patient as a potable concentrated solution of glucose in water. Reported glucose concentrations range generally from about 25% to about 50% (W/V) (3). Currently more than 10 "standard" oral glucose tolerance tests, each with its own method of administration and interpretation, are in use.

After ingesting the glucose, the patient's physiological response to the glucose challenge is evaluated. Generally, this is accomplished by determining the patient's blood glucose levels (the concentration of glucose in the patient's plasma, serum or whole blood) for several predetermined points in time. Several statistical methods have been developed to analyze the blood glucose data obtained, e.g., the Wilkerson point method.

Clinicians have long known that the conditions under which an oral glucose tolerance test is administered will affect the data obtained. In an effort to improve reliability and standardize oral glucose tolerance testing, the Committee on Statistics of the American Diabetes Association (ADA) has recommended standardized conditions under which the tests should be performed. These conditions include that the patient be in good health, maintain a minimum intake of 150 grams of dietary carbohydrates for three days, and fast for at least eight hours, but no longer than sixteen hours, prior to testing. Further, on the day of the test the patient should not smoke, use drugs or exercise, and should avoid undue mental stress. Presently, most oral glucose tolerance tests are administered following a similar protocol. However, even when conditions are closely monitored, oral glucose tolerance tests have yielded inaccurate, and non-reproducible data. Because of the inaccuracy of the test, patients are frequently misdiagnosed as diabetic.

Although they are commonly used throughout the world, oral glucose tolerance tests have been criticized as inaccurate. One published study concluded that patients subjected to repeated oral glucose tolerance tests showed a blood glucose mean difference of 26mg/dl at 1 hour and 20mg/dl at 2 hours. Clinicians, because of results such as these, have proposed that the use of oral glucose tolerance tests be discontinued, suggesting that less harm might be caused by not using the test than by misdiagnosing diabetes with it.

Studies conducted by the present inventors indicate that the glucose concentration of the test solution, the volume of the test solution, and the total dose of glucose administered, all affect patient comfort, test accuracy, and reproducibility of results. Significantly, these are the parameters which vary the most from one clinical group to another. For example, the dose of glucose recommended by the National Institutes of Health (NIH) work group is 75 gm for adults, and 1.75 gm/kg body weight for children, up to about a maximum of 75 gm. According to NIH, NIH chose this amount since a 50 gram glucose dose, previously recommended by the British Diabetic Association, was insufficiently provocative to demonstrate glucose intolerance, whereas a 100 gram glucose dose, recommended by the American Diabetic Association, was associated with symptoms of nausea and vomiting during the test (6).

As discussed above, the glucose dose is generally administered as an aqueous solution. The rate and efficiency of gastrointestinal glucose absorption, and the comfort of the patient being evaluated, depend to a great extent on the concentration (osmolarity) of the glucose solution administered. Researchers have reported that highly concentrated glucose solutions, e.g., 25-50% (W/V), cause gastric irritation, and a delay in gastric emptying time resulting in nausea and vomiting. It is believed that these adverse effects are caused by a gastrointestinal osmotic imbalance (2). This imbalance leads to a disturbance in gastrointestinal glucose absorption which can result nausea and vomiting, and in delayed or incomplete glucose absorption.

Results of a survey of 10 hospitals in the San Antonio, Texas area conducted by the present inventors revealed that when a glucose solution including varying amounts of glucose (75 gm or 100 gm) was administered to adult patients, as required in the standard oral glucose tolerance test, nausea and vomiting were reported in 40-80% of the patients. Of the hospitals surveyed nausea and vomiting was reported in nearly 100% of the pregnant patients-the worst symptoms were seen with "cola" flavored beverages. Researchers have reported that low concentration glucose solutions, e.g., 5-15% necessitate the administration of large volumes of liquid, which, in turn, causes nausea and vomiting, as well as poor gastrointestinal absorption (2).

The data obtained from oral glucose tolerance tests (OGTTs) is used to diagnose diabetes in a patient. However, many different glucose methodologies, i.e., glucose loading dose, solution volume, and glucose concentration, have been utilized in administering oral glucose tolerance tests. These different methodologies result in significant changes in patient comfort and in blood glucose values. This results in confusion in the interpretation of oral glucose tolerance tests. Presently, the oral glucose tolerance test is of questionable value because of the variability of the response in patients. Indeed, several clinicians recommend that the oral glucose tolerance test be abandoned (5).

Although different versions of the oral glucose tolerance test have been in use for almost 200 years, physicians are still unable to identify and classify diabetes with certainty in many individuals. Current oral glucose tolerance tests have numerous documented pitfalls and irregularities with both patient compliance and diagnostic acumen. The problems of the current tests include, but are not limited to, nausea, vomiting, nonreproducible results, and misdiagnosis. Thus, the present invention is generally directed to providing a method for diagnosing diabetes in a human subject which avoids the problems of currently available oral glucose tolerance tests.

Accordingly, there is presently a need for a well-tolerated oral glucose tolerance test which does not cause the nausea and vomiting typically associated with currently available tests. Further, there is a need for an oral glucose tolerance test that will more accurately diagnose diabetes. Lastly, there is also a need for an oral glucose tolerance test which yields consistent, reproducible results.

SUMMARY OF THE INVENTION

The present invention is directed to overcoming the deficiencies inherent in currently available oral glucose tolerance tests. The present invention comprises a method and composition useful in the diagnosis of diabetes in humans and animals. The method of the present invention most generally includes administering a sufficient amount of a well-tolerated potable beverage to a subject being evaluated. The potable beverage of the present invention contains a lower molar concentration and a lower total loading dose of glucose then prior oral glucose tolerance tests. Preferably, the potable beverage includes from about 5 to about 15% glucose (W/V), and a total glucose loading dose of from about 0.35 to about 1.25 grams/kilogram of body weight of the subject being evaluated. As used herein a "sufficient amount" is intended to mean that amount which contains a loading dose of glucose provocative enough to demonstrate glucose intolerance in a subject being evaluated.

Thus one aspect of the present invention is directed to a method for diagnosing diabetes mellitus in a human subject. The method includes the step of administering orally to the subject a sufficient amount of a potable beverage containing from about 5 to about 15% (W/V) glucose. Typically, the inventive method will further include the step of monitoring the level of blood glucose in the subject at predetermined time intervals.

A further aspect of the present invention provides a method which includes the step of administering orally to a subject from about 225 ml to about 675ml of a potable beverage containing from about 5 to about 15% glucose (W/V). Preferably, the total volume of potable beverage administered contains from about 25 to about 50 grams of glucose. According to a preferred embodiment, the potable beverage is administered to the subject after a period of relative fasting of from about 4 to about 10 hours, and is consumed in from about 2 to about 10 minutes.

The inventive method may further include the step of measuring the level of blood glucose in the subject immediately prior to administering the potable beverage, and at 30, 60, 90, and/or 120 minutes thereafter. According to a preferred embodiment, the blood glucose levels are determined at only immediately prior to administration of the potable beverage, and at 30 and 60 minutes thereafter.

A still further aspect of the present invention provides a method which comprises administering to a subject from about 0.35 to about 1.25 grams of glucose per kilogram of body weight as an aqueous glucose solution including from about 5 to about 15% glucose (W/V). According to a preferred embodiment, the method includes administering to the subject about 0.7 grams of glucose per kilogram of body weight as an aqueous glucose solution including from about 10 to about 12% glucose (W/V). In a another embodiment, the method includes orally administering to the subject about 450 ml of an aqueous glucose solution including about 50 grams of glucose.

In still further embodiments, the present invention relates to a unit dose potable beverage which comprises water and glucose which may be used in connection with the foregoing methods. The unit dose will typically comprise a total from about 20 to 60 grams of glucose per unit dose, with the glucose being present in a concentration ranging from about 5 to about 15% (W/V). These unit doses will therefore be specifically adapted for practicing the foregoing methods in that they will provide a convenient dosage form for conducting, for example, the foregoing diagnostic tests.

In more preferred embodiments, the potable beverage will comprise from about 7 to about 12% glucose (W/V) and in still further preferred embodiments, from about 10 to about 12% glucose (W/V). The most preferred concentration will be about 11% glucose (W/V).

Typically, the potable beverage will have a volume from about 225 to about 675 ml. More preferably, the unit dose will comprise a volume from about 350 to about 550 ml, and in still more preferred embodiments, from about 400 to about 500 ml. The most preferred volume for the unit dose of potable beverage will be about 450 ml.

In order to achieve advantages in accordance with more preferred aspects of the invention, the unit dosage of the potable beverage will typically include from about 25 to about 50 grams of glucose, and preferably from about 35 to about 50 grams of glucose. In the most preferred embodiments, the potable beverage will include about a total of about 50 grams of glucose as will be appreciated from the discussions and examples set forth herein below. The administration of these amounts of glucose will not only provide highly reproducible results in a minimal amount of time, but will serve further to reduce the instances of nausea and delayed gastric emptying.

BRIEF DESCRIPTION OF THE DRAWINGS

FIG. 6 is a bar graph representing average gastric half-emptying time in minutes comparing the modified 50 gm modified OGTT and the standard 100 gm OGTT.

FIG. 7 is a bar graph representing average glucose solution remaining in the stomach after 30 and 120 minutes comparing the modified 50 gm modified OGTT and the standard 100 gm OGTT.

FIG. 8 is a bar graph demonstrating that after 2 hours, 43 grams of glucose remained in the stomach using the standard 100 gm OGTT and 10 grams remained using the modified 50 gm modified OGTT.

DESCRIPTION OF THE PREFERRED EMBODIMENTS

Figure 1:
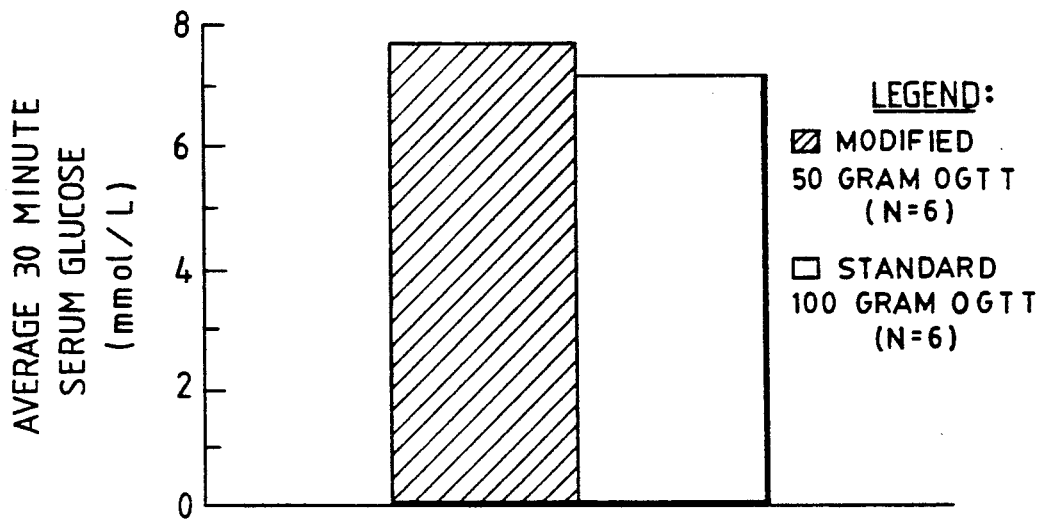
FIG. 1 is a bar graph representing average serum values 30 minutes after ingestion of the standard 100 gm OGTT and the modified 50 gm modified OGTT.

The present invention is directed to the problems inherent in current oral glucose tolerance tests. Studies conducted by the present inventors indicate that oral glucose tolerance tests which include a large loading dose, e.g., greater than about 1.5 grams glucose/kg body weight, and/or a hyperosmolar glucose solution, e.g., greater than about 1.85 ml glucose/L water, tend to produce a large amount of intersubject variability, cause delayed gastric emptying of the glucose solution, as well as the frequently associated nausea and vomiting. The present invention provides a method for diagnosing diabetes in a human subject using a modified oral glucose tolerance test. The methods of the present invention employ a particular potable beverage having a lower osmolar concentration of glucose and a lower total glucose loading dose. Studies have demonstrated that these oral glucose solutions are well-tolerated, allow more rapid gastric emptying, provide more rapid and more complete gastrointestinal glucose absorption, and provide generally high reproducibility of results.

Studies conducted by the inventors indicate that gastric emptying and gastrointestinal absorption are directly related to both the osmolarity of the glucose solution and the total glucose load administered. It is believed that the delayed gastric emptying which is seen with currently available OGTTs makes these tests erratic and decreases their ability to diagnose diabetes accurately. In addition, further studies using the lower osmolar solutions of the present invention have demonstrated their superior performance in diagnosing diabetes. Clinical studies have shown that the methods of the present invention produce a distinct separation between nondiabetic and diabetic subjects. For example, according to one study, the blood sugar of nondiabetic subjects peaked distinctly at about ½ hour, while the blood sugar of diabetic subjects peaked distinctly at about 1 hour or later.

Even though the methods of the present invention will preferably include a glucose loading dose of half or less than about half that of currently available tests, because of the more rapid gastric emptying and better gastrointestinal glucose absorption, these methods deliver an equal or greater amount of glucose to the blood than the currently available oral glucose tolerance tests in the first hour. Through the practice of these methods, one will typically realize both a well tolerated test and one which yields improved accuracy and reproducibility of results. Thus, the methods of the present invention are believed to be superior to currently available methods for diagnosing diabetes in a human subject. It is further believed that the methods of the present invention will more accurately diagnose "prediabetics," "borderline," and "equivocal" diabetics so that the disease can be treated aggressively in its earliest stages in hopse of preventing or minimizing morbidity and mortality.

According to a preferred embodiment of the invention, a potable beverage is provided for consumption by a human subject. The potable beverage preferably includes water, a flavoring agent, and from about 5 to about 15% glucose (W/V). Expressed in other terms, the glucose molar concentration in the beverage is from about 0.28 to about 0.83. More preferably, the potable beverage will include from about 7 to about 12% glucose (W/V). Most preferably, however, the solution will include from about 10% to about 12% glucose (W/V), with approximately a 0.62 molar glucose solution (11.3% glucose (W/V) being most desired.

The potable beverage preferably will include a flavoring agent. It is believed that a flavoring agent will aid in the palatability of the potable beverage. The only limitations on the selection of the flavoring agent are that it should not interfere with the test or interact with the other constituents of the potable beverage. Preferably, flavoring agents which are currently used to flavor available OGTTs may be used in the practice of the present invention, i.e., orange, lemon-lime.

To practice the method of the present invention, it preferable that the subject being evaluated has fasted for from about 4 to about 10 hours prior to the test. Further, a sufficient amount of the beverage is orally consumed by the subject in from about 2 to about 10 minutes, and most preferably in about 5 minutes. In one embodiment, the sufficient amount consumed includes a volume from about 225 to about 675 ml, and a total glucose loading dose of from about 0.35 grams to about 1.25 grams of glucose per kilogram of subject body weight. In a another embodiment, the sufficient amount consumed includes from about 350 to about 550 ml, and a total glucose dose of from about 0.5 to about 1.2 grams of glucose per kilogram of subject body weight. More preferably, the sufficient amount consumed includes from about 400 to about 500 ml, and a total glucose dose of from about 0.60 to about 0.8 grams of glucose per kilogram of subject body weight. According to a most preferred embodiment, however, the sufficient amount includes a volume about 450 ml, and a total glucose loading dose of about 0.7 gram per kilogram of subject body weight.

The sufficient amount can also be expressed as a total loading dose of glucose consumed. According to one embodiment, the sufficient amount consumed includes from about 25 to about 50 grams of glucose. More preferably, the sufficient amount consumed includes from about 35 to about 50 grams of glucose. Most preferably, the sufficient amount consumed includes about 50 grams.

An aspect of the present invention is concerned with providing the lowest sufficient amount of glucose in the smallest volume of potable beverage. According to one preferred embodiment, the sufficient amount consumed includes a volume of no more than about 600 ml, and a total glucose loading dose of from about 25 to a maximum of 60 grams. Another embodiment of the invention will include a volume of no more than about 450 ml, and a total glucose loading dose of from about 35 to about 50 grams. A more preferable embodiment will include no more than about 450 ml, and a total glucose loading dose of about 50 grams.

The subject's insulin response to the glucose challenge is indicative of the presence of diabetes. This response is determined by measuring the subject's blood glucose level before and after glucose administration. Blood glucose levels are measured in whole blood, plasma, or serum, most preferably serum, at various predetermined times during the test. According to one embodiment of the invention, the subject's blood glucose level is determined just prior to administering the glucose beverage (time = 0), and at 30, 60, 90, and 120 minutes thereafter. However, according to the most preferred embodiment, blood glucose levels are determined at time 0, 30 and 60 minutes thereafter. Studies by the present inventors have shown that those individuals whose blood glucose level is the greatest, i.e., peaks at about 30 minutes after administration of the beverage are not diabetic. However, those individuals whose blood glucose level peaks at about 60 minutes after administration of the beverage are diagnosed as diabetic.

Thus, the present invention provides an accurate, and reproducible qualitative method for diagnosing diabetes in a human subject. It should be noted that the present invention can diagnose diabetes in a subject without resorting to one of the many complicated statistical systems presently required for evaluating blood glucose levels and diagnosing diabetes, e.g., the Wilkerson point system. Further, the present invention makes possible the diagnosis of diabetes in as little as one hour, as compared to as much as three to five hours using standard tests presently available. This results in the obvious advantages of lower costs, better patient compliance, ease of administration, and fewer errors in the interpretation of the results.

It is believed that methods of the present invention will provide a useful method for screening adults as well as children for the presence of diabetes. Because of the low total glucose loading dose, it is believed that the methods of the present will not need to be modified to effectively screen a wide range of the population. Further, since the methods of the present invention are well tolerated, it is believed that the screening of pregnant women will be simpler, less expensive, and more widespread. Thus, more patients will be diagnosed earlier, thereby avoiding significant mortality and morbidity.

A further aspect of the present invention is directed to a composition useful in the diagnosis of diabetes in a human subject. The composition of the present invention includes a unit dose sterile potable glucose beverage. The compositions of the present invention provide for ease of administration, greater patient compliance and tolerance, and greater accuracy and reproducibility of results. The potable beverage preferably includes water, a flavoring agent, and from about 5 to about 15% glucose (W/V). Expressed in other terms, the glucose molar concentration in the potable beverage is from about 0.28 to about 0.83. More preferably, the potable beverage will include from about 7 to about 12% glucose (W/V). Most preferably, however, the solution will include from about 10% to about 12% glucose (W/V), with approximately a 0.62 molar glucose solution (11.3% glucose W/V) being most desired.

According to one embodiment, the unit dose potable beverage is unit dose packaged in a bottle including a volume of from about 225 to about 675 ml, and a total glucose loading dose of from about 25 grams to about 50 grams. In a another embodiment, the unit dose container includes from about 350 to about 550 ml, and a total glucose dose of from about 35 to about 50 grams of glucose. More preferably, the unit dose container includes from about 400 to about 500 ml, and a total glucose dose of from about 40 to about 50 grams. Most preferably, however, the unit dose container includes a volume about 450 ml, and a total glucose loading dose of about 50 grams.

According to one embodiment, the compositions of the present invention are prepared using Dextrose USP, also referred to as D-Glucose Monohydrate. Dextrose USP is a odorless crystalline white powder, having a sweet taste, and a solubility in water of about 1 gram per ml. Dextrose USP is preferred to Liquid Glucose USP, since Liquid Glucose USP includes varying amounts of dextrose, dextrins, maltose, and water. It is believed that the inventive method and composition of the present invention will produce more reproducible results if Dextrose USP is utilized in the preparation of the potable beverage. Thus, from 25 to about 50 grams of Dextrose USP is weighed and set aside. The Dextrose USP is then added to from about 225 to about 675 ml of distilled water. The mixture preferably has a glucose concentration of from 5 to about 15% (W/V). Dextrose USP solubilizes quickly in distilled water. However, if needed the mixture may be gently agitated to ensure that the dextrose USP solubilizes. A flavoring agent may also be added to improve the palatability of the beverage. Once prepared, the solution is sterilized. Although several methods are available for sterilizing the solution, preferably the solution is sterilized by cold vacuum filtration through a filter having a pore size diameter of from 0.25 to about 8 microns, and most preferably, about 2 microns. After the solution is sterilized, the solution is aseptically unit dose packaged, preferably in a glass or plastic bottle.

Although the methods and compositions of the present invention will find their greatest utility in the performance of oral glucose tolerance tests in humans, their utility is certainly not limited in this regard. For example, the present inventors contemplate that these methods and compositions will find utility in veterinary applications. Veterinarians currently use the standard osmolar glucose solution used for humans to diagnose diabetes in animals. It is proposed that the modified solutions of the present invention will be much more effective, more reproducible and better tolerated in veterinary applications, just as it is proving to be in human applications.

For veterinary applications, the most ideal dose will still have an osmolarity of from about 0.4 M to 1.0 M, with the most preferred solution being about 0.6 to 0.8 M. Typically, one will want to administer a total dose of on the order of about 0.65 to about 0.75 grams of glucose per kilogram body weight. As in humans, the inventors contemplate that a similar delayed peak of the glucose values will be seen in diabetic animals. This modified solution should demonstrate a better reproducibility because of more rapid gastric emptying and more rapid intestinal absorption.

In the context of human application or perhaps even veterinary, it is contemplated that the reproducibility of these tests is such that will render them directly applicable to mass screening by, e.g., finger stick analysis. It is proposed that the modified solutions of the present invention will be particularly well suited to large scale mass screening of large populations for diabetes and that it will be possible to use finger stick glucose values to determine if a person has type II diabetes or is at risk for the development of type II diabetes.

The basis for this proposition is at least four fold. First, the modified solution is more physiologic and therefore better tolerated without associated nausea and vomiting. Of course, this is important where one seeks to obtain wide spread compliance. Secondly, the shape of the glucose curve that is obtained following administration of the modified solutions obviates the need for the exact quantification to determine if a person is a diabetic. This alleviates the problem of decrease accuracy found with the finger stick methods that are currently available. The use of the curve shape to determine a glucose peak at 30 minutes from a finger stick glucose determination should allow for sensitive diabetes screening.

The third advantage of the modified solution for wide spread screening purposes is that it can readily be completed within one hour, without the need for four and even five hour regimens which are required for the current OGTT. The glucose values at zero, 30, and 60 minutes from three finger sticks could be compared and the shape of the curves assessed in 1 hour. In fact, one can simply correlate this data to a ratio which compares the glucose level at the 30 minute time point to the glucose level at the 60 minute time point. In this regard, individuals receiving the modified solutions of the present invention at time zero, who demonstrate a hiqher qluoose level at the 30 minute time period as oompared to the 60 minute time period, would not be oonsidered diabetio. Conversely, individuals exhibiting a higher glucose level at the 60 minute time point in relation to the 30 time point would be considered a likely diabetic.

The fourth advantage is that the methods of the present invention could be very inexpensive. The cost of a finger stick glucose and the glucose solution which contains one-half of the glucose of the standard solutions could be performed for very small amount of money.

The inventors further contemplate that the modified solutions of the present invention can be employed as a screening method for insulin resistance. It has recently been proposed by authorities on type II diabetes that insulin resistance not associated with diabetes may nevertheless lead to potentially serious health complications, including an increased risk of coronary artery disease and hypertension (8–10). Initial studies have found insulin resistance to be common in patients with hypertension and coronary artery disease. There is even speculation that insulin resistance may be an initial lesion in the development of these different diseases (8, 9). Furthermore, Reaven has termed this association of insulin resistance "Syndrome-X", and describe seemingly healthy people who have insulin resistance, display a cluster of coronary risk factors including high blood pressure, elevated triglycerides and decreased levels of high density lipoproteins or HDL (10).

Presently, insulin resistance can be screened for by checking a fasting serum insulin level. Unfortunately, this test is both expensive and it does not demonstrate the body's response to a glucose load. It is proposed that the modified solutions of the present invention will provide an excellent screening test for the detection of insulin resistance. For example, if the glucose value peaks at one hour or later, and in spite of fairly low glucose values, this should be representative of insulin resistance. This is the same phenomena that is detected in the diagnosis of type II diabetes, but without the high elevations of blood sugar.

An inexpensive means of screening for insulin resistance is important because current research indicates that insulin resistance or elevated plasma insulin levels are the earliest markers of a higher risk of coronary artery disease mortality (9). Thus, an inexpensive means of screening for early coronary artery disease risk could lead to major preventative treatment and a reduction in overall mortality from coronary artery disease, the number one cause of death in the United States. It is proposed that the modified solution should be given in the same manner as for the diabetes diagnosis, with blood samples at zero, 30 and 60 minutes by finger stick or venipuncture. A flattened or delayed peak will indicate insulin resistance and a delayed response to the glucose load.

As has been discussed above, the modified glucose solutions of the present invention provide particular advantages over the previously used solutions in that they do not delay gastric emptying in the manner of the prior solutions. Thus, the modified glucose solutions of the present invention are particularly useful for studying gastric emptying. The glucose in these solutions result in the emptying of solutions from the stomach in a very reproducible manner in normal subjects. For example, normal subjects empty approximately 0.42 to 0.5 grams of glucose per minute from their stomachs. This corresponds to a glucose energy equivalent of about 1.7 to 2.0 kcal per minute. Gastric emptying studies are often employed to detect delayed gastric emptying which is a frequent complication of late diabetes. Gastric emptying studies now account for approximately 5 percent of all nuclear medicine studies.

One of the problems with currently used studies is that there is no standardization of gastric emptying. Some institutions employ radiolabeled chicken liver, some use labeled scrambled egg, and other use corn flakes. Because of this lack of standardization, it is impossible to compare gastric emptying studies from one institution to another. Each institution currently makes up their own solution or meal, and studies at least 20 volunteers to determine the normal range.

There is currently no standardized liquid or solid on the market for use in gastric emptying studies. The modified solutions of the present invention will typically have a standardized amount of glucose in a standard volume of water with values of normal emptying time precharacterized for the particular solution. Because the normal half-emptying time with the modified solutions of the present invention is about 50 to 60 minutes, the modified solution is ideal for clinical gastric emptying studies, in that the practical time limit for performing these studies is about one hour. The current 100 gram high osmolar glucose solution that is used for glucose tolerance testing has a half-time greater than 105 minutes in normal volunteer and is therefore not particularly practical for gastric emptying studies. The prior solutions also do not comprise a physiologic glucose concentration and is therefore associated with nausea and vomiting.

A standardized solution will solve many of the problems of performing the gastric emptying studies in community hospitals where convenience is important and determination of normal values for the test using, for example, 20 normal volunteers, is not practical. The present test would allow easy determination of normal versus abnormal gastric emptying. The data can readily be reported in kcal per minute or in grams of glucose per minute emptying time. Currently, gastric emptying studies cannot be reported in this manner due to variability in calories contained in eggs, cereal or liver.

The use of the present solutions in the context to gastric emptying studies is particularly important in tha it has not been previously recognized that liquid glucose solutions will delay gastric emptying solution to the extent that they do. For example, nuclear medicine physician generally assume that all liquids will empty half of their contents from the stomach in less than 30 minutes. By comparison, the half emptying time of the modified glucose solutions of the invention are typically 50 to 60 minutes.

Furthermore, due to the excellent interpatient and intrapatient population reproducibility of gastric emptying as well as blood glucose levels achieved with the solutions of the present invention, it is proposed that these solutions will prove to be ideal in the diagnosis of a variety of glucose-related disorders, for example, gestational diabetes, insulin resistance, impaired glucose tolerance, gastric emptying in diabetic patients (who typically will exhibit delayed gastric emptying after several years), and even diabetes and related disorders in animals.

The following examples are presented to describe preferred embodiments and utilities of the present invention and are not meant to limit the present invention unless otherwise stated the claims appended hereto.

EXAMPLES

EXAMPLE 1

Sixteen subjects were studied using an oral glucose solution of the present invention (modified OGTT) and a glucose solution typically used in standard oral glucose tolerance tests (standard OGTT). The composition of these solutions are discussed herein below. All sixteen subjects were between 27 and 42 years old, and all had been fasting for more than 10 hours prior to beginning each test. Four subjects were known (type II) diabetics. Standard OGTTs were also administered to six of the nondiabetic subjects. Written consent was obtained from the subjects after the nature of the procedure was explained and prior to testing.

"Glucose Tolerance Test Beverage®," lemon-lime flavor (General Scientific, Richmond, VA) was used for both the standard and modified OGTTs. For the standard OGTT, 100 grams of glucose (1.85 mol/L - the entire 300 ml bottle) was ingested by the patient within 5 minutes. For the modified OGTT, 50 grams of glucose (½ the 300 ml bottle) mixed with 300 mL of water (0.62 mol/L) was ingested by the patient within 5 minutes. The total volume ingested was 450 ml. Blood samples were drawn at 0, 30, 60, 90 and 120 minutes following ingestion of the glucose solutions.

Serum glucose was measured with the "Paramax" instrument (Baxter Healthcare Corp., Irvine, CA 92718-2017) by a modification of the coupled enzymatic method of Stein (7). The modifications involve the use of NAD. and glucose-6-phosphate dehydrogenase (G-6-PDH) from *Leuconostoc mesenteroides* rather than yeast. Glucose is phosphorylated to glucose 6-phosphate in the presence of hexokinase, converted to 6-phosphogluconate in the presence of G-6-PDH, and NAD was reduced to NADH, causing a change in absorbance, which was monitored bichromatically at 340/405 nm. The assay temperature was 37° C.

RESULTS

Serum glucose levels were evaluated in six of the nondiabetic subjects during both the standard and modified OGTT (FIG. 1). Even though less glucose was administered with the modified 50 gram OGTT, the 30 minute serum glucose levels consistently peaked higher than with the standard 100 gram OGTT.

Moderate to severe nausea was experienced frequently when the standard OGTT was administered to subjects. Each of the 16 times the modified OGTT was administered, no nausea was reported.

Figure 2:
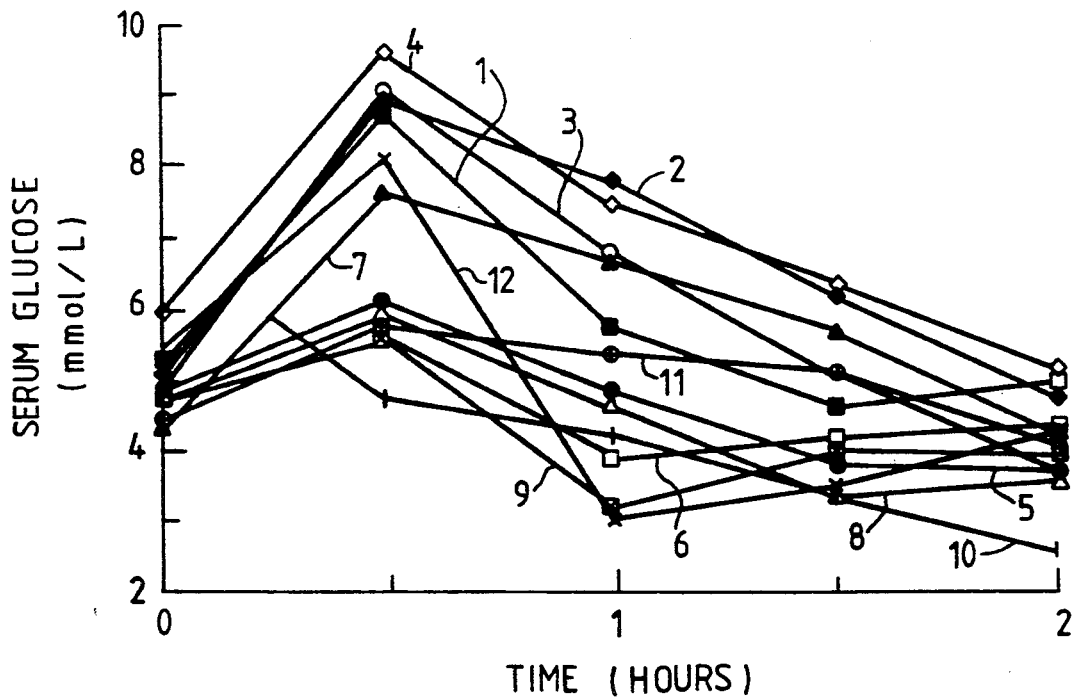
FIG. 2 is a graphic representation of the serum glucose levels over time of twelve nondiabetic subjects using the modified 50 gm glucose solution. The graph shows that all the subjects had consistently higher serum glucose levels at one-half hour compared to their one hour serum glucose level.
Figure 3:
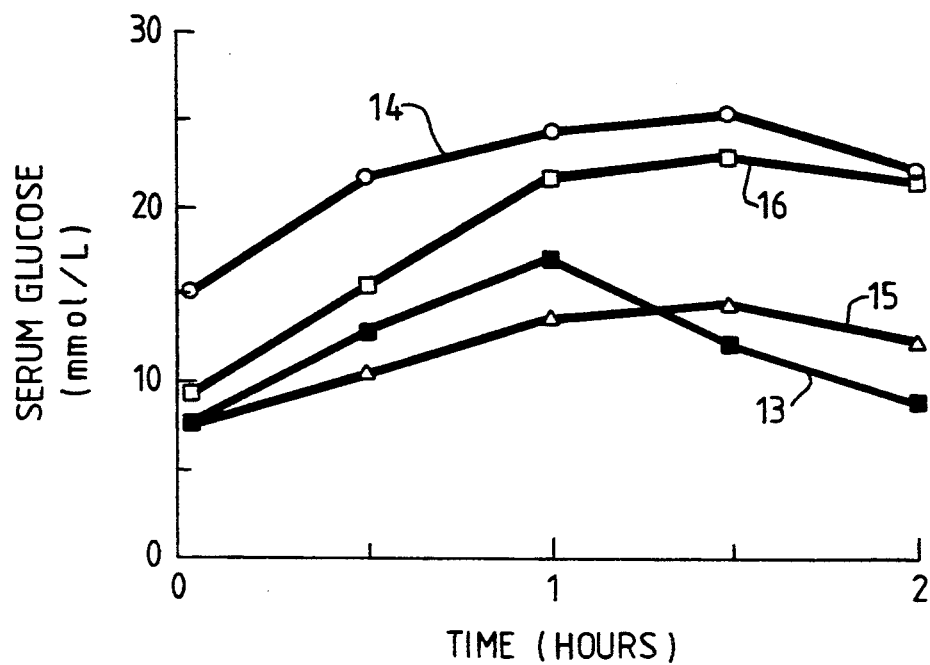
FIG. 3 is a graphic representation of the serum glucose level over time of four diabetic subjects using the modified 50 gm glucose solution. The graph shows that all the subjects had consistently higher serum glucose levels at one hour compared to their one-half hour serum glucose level.

Surprisingly, it was determined that in nondiabetic subjects, after the administration of the modified OGTT, serum glucose levels were consistently higher at one-half hour compared to the one-hour serum glucose level (FIG. 2). In the type II diabetic subjects, the serum glucose levels consistently peaked at 1 hour or later using the modified OGTT (FIG. 3). FIGS. 2 and 3 also demonstrate the consistency of the modified OGTT, possibly as a result of the more rapid gastric emptying.

Figure 4:
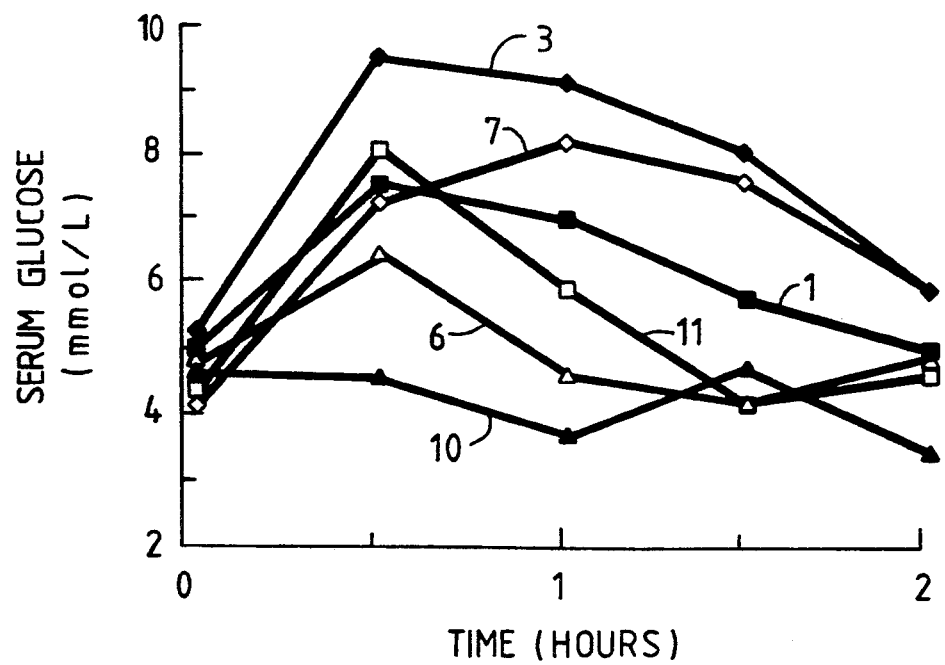
FIG. 4 is a graphic representation of the serum glucose levels over time of six nondiabetic subjects using the standard 100 gm glucose solution. The graph shows that all the subjects had marked variability in their serum glucose levels.
Figure 5A:
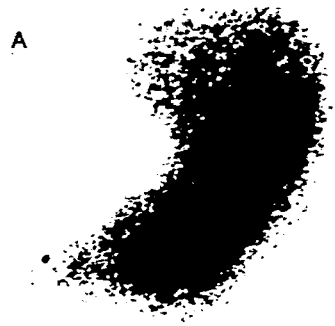
FIG. 5 is a gamma camera scan of gastric emptying. Figure A is an image 5 minutes after ingestion of the modified OGTT. Figure B is an image 90 minutes after ingestion of the modified OGTT. Figure C is an image 5 minutes after ingestion of the standard OGTT. Figure D is an image 90 minutes after ingestion of the standard OGTT.
Figure 5B:
Figure 5C:
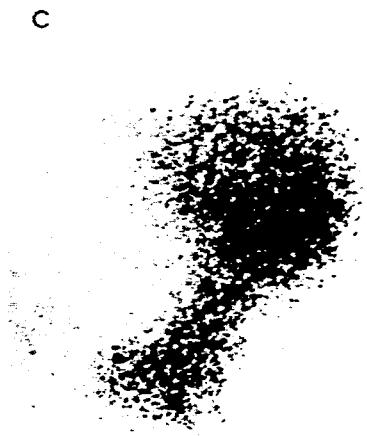
Figure 5D:

FIG. 4 illustrates the marked intersubject variability using the standard 100 gram OGTT on nondiabetic subjects. This aspect of the standard OGTT has been noted by other authors (5).

EXAMPLE 2

Gastric emptying studies were conducted using radiolabeled glucose. The studies were conducted to determine the comparative rates at which standard OGTTs and the modified OGTTs solutions were emptied from the stomach into the intestine. Gastric emptying studies utilizing a gamma camera (Scintronix USA Inc., Woburn, MA) were performed on four nondiabetic subjects. The subjects were administered both the modified and standard OGTTs . The studies were conducted at least one week apart to prevent any residual radioactive material from interfering with the interpretation of the nuclear scan. Approximately 200 uCi of 99 metastable technetium sulfur (99mTc-Sc, CIS-US, Bedford, MA) was added and mixed with each glucose solution. The subjects drank the glucose solutions in their entirety within 5 minutes shortly after the 99m Tc-Sc had been added to the solution.

The subjects were then placed in a semi-reclining position (45° from horizontal) and the gamma camera was positioned anteriorly. Data was collected continuously and summed at 30 second intervals. Images were acquired until at least half of the glucose solution had emptied from the subjects' stomachs. Blood samples were drawn at 0, 30, 60, 90 and 120 minutes following ingestion of the glucose solution. The blood was collected in vacutainer tubes containing potassium oxalate and sodium fluoride (Becton Dickinson Vacutainer Systems, Rutherford, NJ). Glucose analysis was performed on a Paramax instrument (Baxter Healthcare Corp., Irvine, CA).

The Scintronix gamma camera was used with a low-energy, all purpose collimator at a 20% window setting centered at 140 keV. The camera was connected to a Medical Data Systems Computer (Ann Arbor, MI). A region of interest corresponding to the stomach was selected. Counts in the stomach region of interest were calculated in each 30 second image. After correcting for radioactive decay, the count rate of the regions of interest were converted to percent of the maximum count rate recorded.

RESULTS

Gastric emptying was inhibited using the standard OGTT when compared to the modified OGTT as seen in FIGS. 5A through 5D. FIG. 6 indicates that the half-emptying time was approximately twice as long (97.5 minutes) with the standard OGTT compared to the modified glucose solution (58 minutes). Thirty minutes after ingestion of the standard oral glucose solution, the nondiabetic subjects had 80% or more of the glucose solution remaining in their stomachs; 69% remained with the modified solution. After two hours 43% of the standard glucose solution remained in the stomach of the nondiabetic subjects; 19% remained using the modified solution (FIG. 7). More rapid gastric emptying was observed with the modified glucose solution, allowing glucose to enter the peripheral circulation at a faster rate. FIG. 8 demonstrates that 43 grams of glucose remained in the stomach after two hours with the standard glucose solution; 10 grams of glucose remained with the modified solution.

Utilizing half-emptying time data from the gastric emptying studies, it was calculated that 1.90 kcal/min were delivered to the duodenum with the standard OGTT, while 1.92 kcal/min were delivered with the modified OGTT. 1.5 ml/min was emptied from the stomach using the standard OGTT; 4.5 ml/min was emptied with the modified OGTT.

EXAMPLE 3

After a 10 hour fast, one nondiabetic volunteer and one type II diabetic were initially given the standard 100 gm of glucose in 300 mL of water (one bottle of Glucose tolerance Test Beverage) to which had been added 200 $\mu$Ci of 99m Tc-Sc. A gastric emptying study with nuclear imaging was then performed as described in Example 2, with blood being drawn simultaneously according to the standard OGTT protocol described in Example 1.

One week later the modified OGTT was administered according to the protocol described in Example 1 to the same two volunteers while the gastric emptying study was being performed according to the protocol described in Example 2.

RESULTS

Figure 9:
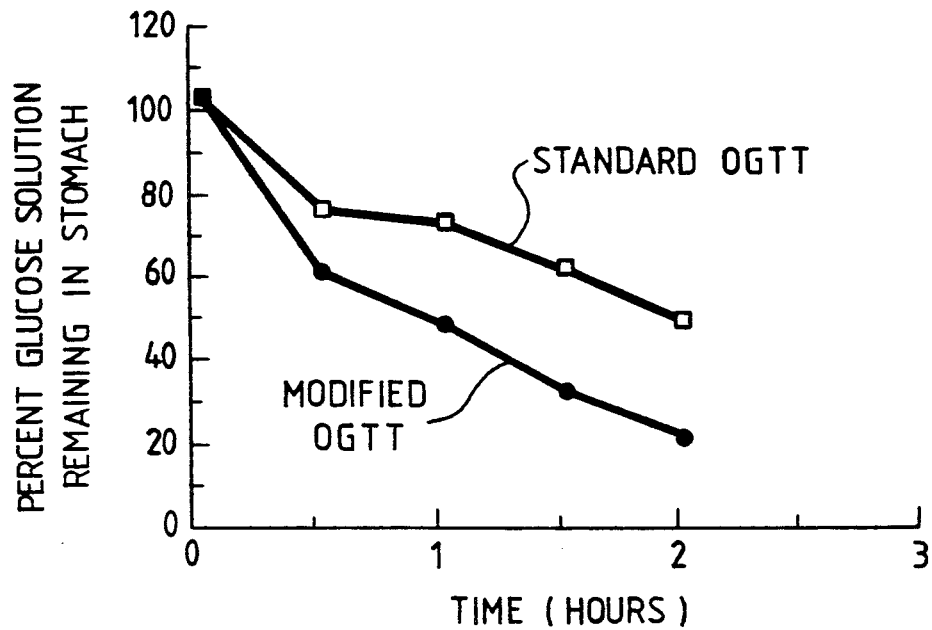
FIG. 9 is a graphic representation of gastric emptying versus time in a nondiabetic volunteer comparing the gastric emptying of the modified 50 gm modified OGTT and the standard 100 gm OGTT.
Figure 10:
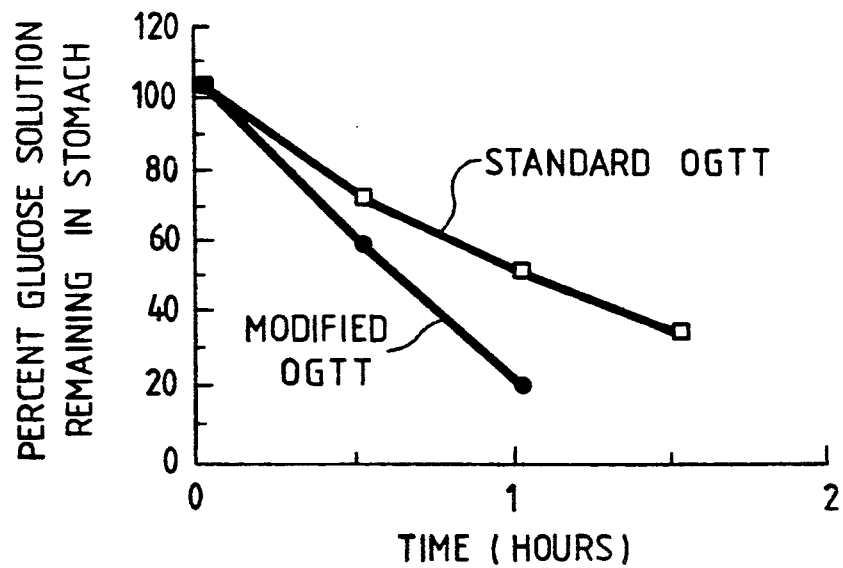
FIG. 10 is a graphic representation of gastric emptying versus time in a type II diabetic volunteer comparing the gastric emptying of the modified 50 gm modified OGTT and the standard 100 gm OGTT.

Gastric emptying was inhibited by the standard OGTT as compared with the modified OGTT, as seen in FIGS. 9 and 10. Although gastric emptying was faster for the diabetic volunteer, both the nondiabetic and the diabetic subjects had 50% or more of the standard oral glucose solution in their stomach an hour after the solution was ingested. Much more rapid gastric emptying was observed with the modified solution, allowing glucose to enter the peripheral circulation faster. The half emptying time was approximately twice as long with the standard OGTT (105 min) as with the modified OGTT (52 min) in the nondiabetic volunteer. Although the type II diabetic volunteer had a faster gastric emptying time (by 15 min) than did the nondiabetic volunteer, it was noted that his serum glucose peaked 30 minutes later than did the nondiabetic's.

EXAMPLE 4

Four known type II diabetics and nine nondiabetic volunteers were given the modified OGTT in the early morning, after a 10 hour fast. Blood was drawn from the seated volunteers at 0, 30, 60, 90 and 120 min after they ingested the glucose solution.

RESULTS

The volunteers experienced moderate to severe nausea each time the standard OGTT was administered as compared with no nausea on any of the 13 times the modified OGTT was administered.

It was determined that in the nondiabetic volunteers, the serum glucose concentrations consistently peaked at 30 minutes with the modified OGTT. In the type II diabetic volunteers given the modified OGTT, the serum glucose consistently peaked a 1 hour or later. Using the modified OGTT and Wilkerson's point system, it was possible to diagnose diabetes in the diabetic patients. The interperson variability seen for the modified OGTT was significantly less as compared with FIG. 4 in which this aspect of the standard OGTT was examined.

EXAMPLE 5

After a 10 hour fast, one nondiabetic volunteer was initially given the standard 100 gm of glucose in 300 mL of water (one bottle of Glucose tolerance Test Beverage) to which had been added 200 $\mu$Ci of 99m Tc-Sc. A gastric emptying study with nuclear imaging was then performed as described in Example 2, with blood being drawn according to the standard OGTT protocol described in Example 1.

One week later the modified OGTT was administered according to the protocol described in Example 1 to the same nondiabetic volunteer and one type II diabetic volunteer. A gastric emptying study was being performed according to the protocol described in Example 2. The procedure was repeated one week later on the nondiabetic volunteer in order to evaluate the reproducibility of the test.

RESULTS

Gastric emptying was inhibited by the standard OGTT as compared with the modified OGTT, as seen in Table 1. Although gastric emptying was faster for the diabetic volunteer, both the nondiabetic and the diabetic subjects had less then 50% of the modified oral glucose solution in their stomach an hour after the solution was ingested. Much more rapid gastric emptying was observed with the modified solution, allowing glucose to enter the peripheral circulation faster. The half emptying time was approximately twice as long with the standard OGTT as with the modified OGTT in the nondiabetic volunteer.

TABLE 1

Gastric Emptying Studies[a] Using Standard and Modified Oral Glucose Tolerance Tests
% Glucose Solution Remaining in Stomach

| | Volunteer 1 (nondiabetic) | | |
|---|---|---|---|
| Time (min) | Standard OGTT | Modified 50 g | Modified 50 g |
| 0 | 100 | 100 | 100 |
| 15 | 83 | 72 | 73 |
| 30 | 73 | 58 | 58 |
| 45 | 70 | 56 | 56 |
| 60 | 70 | 45 | 45 |
| 75 | 61 | —[b] | 37 |
| 90 | 58 | — | 29 |
| 105 | 50 | — | 22 |
| 120 | 44 | — | 18 |

| Volunteer 2 (type II diabetic) Modified 50 g OGTT |
|---|
| 100 |
| 74 |
| 56 |
| 34 |
| 17 |

[a]All results have been decay corrected.
[b]Scan not performed.

As seen in Table 2 serum glucose peaked at about 30 minutes in the nondiabetic volunteer (volunteer 1), while serum glucose peaked at about 60 minutes in the diabetic volunteer (volunteer 2). Table 2 also demonstrates the reproducibility of the inventive method. Note that the results obtained in both trials conducted using the modified OGTT on the nondiabetic volunteer are virtually the same. It is believed that results such as this will help alleviate the problem of misdiagnosis seen using standard OGTT.

TABLE 2

Serum Glucose Results with the Standard and Modified OGTT

| | Non Diabetic Volunteer 1 | |
|---|---|---|
| Standard 100 g Glucose OGTT | Modified 50 g OGTT (mmol/L) | Repeat, Modified 50 g OGTT (mmol/L) |
| 0 hr 5.10 | 4.55 | 5.88 |
| ½ hr 9.33 | 9.16 | 9.71 |
| 1 hr 8.99 | 6.83 | 7.55 |
| 2 hr 7.83 | 5.16 | 3.22 |
| 3 hr 5.77 | 3.72 | 3.44 |

| Type II Diabetic Volunteer 2 | |
|---|---|
| 100 g Standard OGTT (mmol/L) | Modified 50 g glucose OGTT (mmol/L) |
| 6.61 | 7.22 |
| 10.66 | 12.10 |
| 16.21 | 16 32 |
| 16.82 | 11.49 |
| 17.09 | 8.22 |

The majority of standard oral glucose tolerance tests continue to reflect the belief that more is better—that is, the more glucose administered, the more accurate the test for diabetes. This belief has resulted in the administration of large amounts of glucose administered in nonphysiologic hyperosmolar solutions. Using gastic emptying studies, tests of the present invention demonstrate several limitations of hyperosmolar glucose solutions. The examples above demonstrate that the more concentrated, higher osmolar solution of glucose actually empties slower from the stomach than the lower osmolar solution. This limitation results in the standard OGTT having a more prolonged delivery of glucose to the peripheral blood. The modified solutions of the present invention deliver a much more compact bolus of glucose to the intestine, and this quick delivery provides a clearer separation between normals and patients with abnormal glucose tolerance. Therefore, it is believed that the methods of the present invention will allow a much more sensitive detection of early insulin resistance in the development of diabetes.

Tests of the present invention also indicated that the current standard OGTT was unreliable because of the variability and non-reproducibility of results, and further, the high incidence of nausea and vomiting associated with the standard OGTT. Nausea and vomiting were completely eliminated using the methods of the present invention. Possibly, this is attributable to a more rapid gastric emptying time compared to the standard OGTT which was observed by nuclear scan.

A surprising and unexpected result achieved using the methods of the present invention was that the serum glucose levels of nondiabetic subjects consistently "peaks" at about 30 minutes, while the serum glucose levels of diabetics consistently "peaks" at about 60 minutes. It is anticipated that this pattern can be established as a recurrent trend with a larger population. The glucose solutions of the present invention deliver glucose to the peripheral circulation serum at an initial rate greater than or equal to the standard OGTT. It would be expected that this delivery should result in similar peak glucose values at 30 minutes for both the present invention and the standard OGTT. However, the present invention delivers a more compact bolus of glucose as compared to the standard OGTT; therefore allowing better differentiation between normal and abnormal insulin responses. Thus, according to one preferred embodiment of the present invention, serum glucose samples are taken 0, 30, and 60 minutes after ingestion of the glucose solution. When the glucose "peak" occurs it is thus used to establish a diagnosis; normals peaking at 30 minutes and diabetics peaking at 60 minutes or later. Accordingly, it is believed that diabetes or prediabetics can be diagnosed earlier, more accurately, and with less morbidity by practicing the methods of the present invention.

EXAMPLE 6

Various studies were performed on normal, non-diabetic subjects to demonstrate the utility of glucose solutions prepared to reflect a variety of concentrations and total unit amounts of glucose. These studies were further undertaken in order to demonstrate the reproducibility of blood levels obtained with solutions falling within preferred ranges, and the tendency of solutions falling outside the preferred ranges to elicit nausea as a side effect. The solutions employed in the following tests were prepared starting with a standard, commercially available glucose solution for OGTT (Glucose Tolerance Test Beverage ®), which was diluted with the indicated amount of water to achieve the indicated glucose osmolarity.

In one study, 60 grams of glucose, represented by 180 cc of the standard glucose solution, was admixed with 270 cc of water to obtain a total volume of 450 cc of solution. The osmolarity of the solution was 0.74 M. The serum glucose levels that were obtained in a fasting subject are set forth below, with the time being measured from the zero minute time point when the modified glucose solution was administered:

| Minutes Following Glucose Administration | Serum Glucose Levels (mg/dL) |
| --- | --- |
| 0 | 78 |
| 30 | 114 |
| 60 | 66 |
| 90 | 84 |
| 120 | 92 |

As can be seen from the foregoing, in this normal subject the serum glucose level peaked at 30 minutes.

Another study was performed using the same modified glucose solution (450 cc total volume, 0.74 M osmolarity) in a second non-diabetic subject. The blood glucose levels obtained this subject at the various time points are as follows:

| Minutes Following Glucose Administration | Serum Glucose Levels (mg/dL) |
| --- | --- |
| 0 | 88 |
| 30 | 119 |
| 60 | 104 |
| 90 | 74 |
| 120 | 83 |

As with the previous study, the blood glucose level was found to peak in this non-diabetic subject at 30 minutes.

Another study was performed employing a glucose solution that was slightly more than one-half the osmolarity of the previous glucose solution. In this study, the modified glucose solution was prepared by admixing 100 cc of the standard glucose solution (33 grams glucose) with 350 cc of water to obtain a final volume of 450 cc and an osmolarity of 0.4 M. Following administration of this solution to a non-diabetic subject, the following serum glucose levels were obtained:

| Minutes Following Glucose Administration | Serum Glucose Levels (mg/dL) |
| --- | --- |
| 0 | 92 |
| 30 | 135 |
| 60 | 118 |
| 90 | 75 |
| 120 | 73 |

As with the 0.74 M osmolar solutions, the 0.41 M solution provided a peak of serum glucose levels at 30 minutes.

The 0.41 osmolar solution studies were performed in a second subject and the following results obtaines:

| Minutes Following Glucose Administration | Serum Glucose Levels (mg/dL) |
| --- | --- |
| 0 | 87 |
| 30 | 134 |
| 60 | 87 |
| 90 | 75 |
| 120 | 75 |

Again, a peak in serum glucose levels was observed at 30 minute time point.

A further study was performed using a fairly high osmolar solution. In this study, 300 cc of the standard glucose solution (100 g) was admixed with 150 cc of water to obtain a 450 cc glucose solution having an osmolarity of 1.23 M. This solution was administered to a non-diabetic subject and the following serum glucose levels obtained:

| Minutes Following Glucose Administration | Serum Glucose Levels (mg/dL) |
| --- | --- |
| 0 | 96 |
| 30 | 152 |
| 60 | 125 |
| 90 | 94 |
| 120 | 105 |

While the glucose level was again observed to peak at the 30 minute time point, the subject complained of significant degree of nausea.

Another study was performed employing a 0.93 osmolar glucose solution prepared by admixing 225 cc of the standard glucose solution (75 g) with 225 cc of water. The results obtained are as follows:

| Minutes Following Glucose Administration | Serum Glucose Levels (mg/dL) |
| --- | --- |
| 0 | 88 |
| 30 | 160 |
| 60 | 125 |
| 90 | 118 |
| 120 | 110 |

As with the 1.23 osmolar solution, the serum glucose level again peaked at 30 minutes, but the subject again complained of a significant degree of nausea.

Studies were then performed using a total of 50 grams of glucose administered as a 0.62 osmolar solution. The solutions were prepared by admixing 150 cc of the standard glucose solution (50 g) with 300 cc of water. The results that were obtained are as follows:

| Minutes Following Glucose Administration | Serum Glucose Levels (mg/dL) |
| --- | --- |
| Subject 1 | |
| 0 | 82 |
| 30 | 165 |
| 60 | 123 |
| 90 | 93 |
| 120 | 67 |
| Subject 2 | |
| 0 | 106 |
| 30 | 175 |
| 60 | 136 |
| 120 | 94 |

As can be seen, in both studies a peak in serum glucose levels at 30 minutes was observed, with the peak being significantly higher than the 60 minutes or 0 minute time point.

An additional study was performed using a high osmolar solution (1.85 M) and a high loading dose (100 g). This study was performed by simply using 300 cc of the standard glucose solution, without dilution with water. The results obtained were as follows:

| Minutes Following Glucose Administration | Serum Glucose Levels (mg/dL) |
| --- | --- |
| 0 | 87 |
| 30 | 132 |
| 60 | 123 |
| 90 | 101 |
| 120 | 87 |

As With the previous studies in employing high-osmolar solutions, while a peak in serum glucose level was seen at minutes, the subject complained of a significant degree of nausea.

From the foregoing studies, it is apparent that the 33, 50 and 60 gram loading dose of glucose gave a clear distinction between the 30 and 60 minute time point and, further, did not lead to the development of nausea in the subject being tested. Nausea was noted in using a 75 gram glucose loading dose (0.93 osmolar) as well as with the 100 gram solutions (1.23 and 1.85 osmolar solutions).

While the invention is susceptible to various modifications and alternative forms, specific embodiments thereof have been shown by way of example and described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

Citations in the following list are incorporated in the pertinent part by reference herein for the reasons cited in the text.

REFERENCES

1. Chandalia, H.B., et al., Diagnosis of diabetes, the size of The carbohydrate load, *Diabetes,* 19:863, 869, 1970.
2. Puyn, U, et al., Glucose and a oligosaccharide glucose tolerance test, *Mschr. kinderheilk,* 124:147, 152, 1977.
3. Sisk, C.W., et al., comparison of the 50 and 100 gram oral glucose tolerance test, *Diabetes,* 19:852, 862, 1970.
4. Klimt, C.R., et al., Standardization of the oral glucose tolerance test, *Diabetes,* 18:229, 1969.
5. Nelson, R. L., Oral glucose tolerance test: Indications and limitations, *Mayo Clinic Proc.,* 63:263, 269, 1988.
6. Busick, E. J., Natural History and Diagnosis, In: Clinical Diabetes Melitus (G. P. Kozak, W. B. Saunders Co., Philadelphia, 1982 ed.)
7. Stein, M. W., D-Glucose: Determination with hexokinase and Glocuse-6-phosphate dehydrogenase methods of enzymatic analysis. New York: Academic Press, 1963:117-123.
8. Foster, D. W., Insulin resistance - a secret killer?, *New Engl. Nrnl. Med.,* 320:733, 1989.
9. Fackelmann, K. A., Hidden heart Lizards, Do high blood insulin level foretell heart disease?, *Science News,* 136:184, 1989.
10. Reaven, G. M., Role of insulin resistance in human disease, *Diabetes,* 37:1595, 1988.

What is claimed is:

1. A method for the diagnosis of diabetes, the method comprising the steps of:
   (a) preparing a single aqueous unit dosage oral glucose composition having from about 25 to about 60 grams of glucose, and a concentration ranging from 5 to 14.4% (W/V) glucose, in an aqueous volume of from about about 225 to about 675 milliliters;
   (b) orally administering said aqueous unit dosage glucose composition to a subject suspected of having diabetes, the amount administered providing from about 0.35 to about 1.25 grams of glucose per kilogram of body weight to the subject; and
   (c) monitoring the blood glucose level in said subject after a predetermined time interval of an hour or less to diagnose diabetes in the subject.

2. The method of claim 1, wherein said unit dosage composition comprises from about 35 to about 50 grams of glucose.

3. The method of claim 2, wherein said unit dosage composition comprises about 50 grams of glucose.

4. The method of claim 1, wherein said unit dosage composition comprises from about 0.50 to about 1.20 grams of glucose per kilogram of body weight of said subject.

5. The method of claim 4, wherein said unit dosage composition comprises from about 0.80 to about 1.10 grams of glucose per kilogram of body weight of said subject.

6. The method of claim 5, wherein said nit dosage composition comprises about 1 gram of glucose per kilogram of body weight of said subject, up to a maximum of 50 grams of glucose per unit dosage.

7. The method of claim 1, wherein said composition further comprises a flavoring agent.

8. The method of claim 1, wherein said subject is an adult human subject.

9. The method of claim 1, wherein the subject is suspected of having type II diabetes.

10. The method of claim 1, wherein said unit dosage glucose composition comprises from about 7% to about 12% glucose (W/V).

11. The method of claim 10, wherein said unit dosage glucose composition comprises from about 10 to about 12% glucose (W/V).

12. The method of claim 11, wherein said unit dosage glucose composition comprises about 11% glucose. (W/V).

13. The method of claim 1, wherein from about 350 to about 550 milliliters of said glucose composition is administered to said subject.

14. The method of claim 13, wherein from about 400 to about 500 milliliters of said glucose composition is administered to said subject.

15. The method of claim 1, wherein said predetermined time interval comprises 30, 45 or 60 minutes following administration of the unit dosage glucose composition.

16. The method of claim 1, wherein a positive diagnosis for diabetics comprises identifying patients who, after ingesting said single unit dosage glucose composition following a period of relative fast, exhibit a peak in their blood glucose level more than thirty minutes following ingestion.

17. The method of claim 1 wherein a negative diagnosis for diabetes comprises identifying patients who after ingesting said single unit dosage glucose composition following a period of relative fast, exhibit a peak in their blood glucose level at thirty minutes or less following ingestion.

18. The method of claim 1, wherein the blood glucose level of the subject is monitored through the use of blood obtained by finger stick.

19. The method of claim 1, wherein said aqueous unit dosage glucose composition is packaged in a unit dosage container.

20. The method of claim 1, wherein an appropriate amount of nonaqueous glucose is prepackaged in a unit dosage container so as to allow the preparation of said aqueous unit dosage composition upon the addition of water.

21. A method for the diagnosis of diabetes, the method comprising the steps of:
  (a) preparing a single aqueous unit dosage oral glucose composition having from about 25 to about 60 grams of glucose, and a concentration ranging from 5 to 14.4% (W/V) glucose, in a aqueous volume of from about 225 to about 675 milliliters;
  (b) orally administering aqueous unit dosage glucose composition to a subject suspected of having diabetes, the amount administered providing from about 0.35 to about 1.25 grams of glucose per kilogram of body weight to the subject; and
  (c) monitoring the blood glucose level in said subject after a predetermined time interval of one hour or less to diagnose diabetes in the subject.

22. A method for the diagnosis of insulin resistance, the method comprising the steps of:
  (a) preparing a single aqueous unit dosage oral glucose composition having from about 25 to about 69 grams of glucose, and a concentration ranging from 5 to 14.4% (W/V) glucose, in a aqueous volume of from about 225 to about 675 milliliters;
  (b) orally administering said aqueous unit dosage glucose composition to a subject suspected of being insulin resistant, the amount administered providing from about 0.35 to about 1.25 grams of glucose per kilogram of body weight to the subject; and
  (c) monitoring the blood glucose level in said subject after a predetermined time interval of one or less to diagnose insulin resistance in the subject.

* * * * *